United States Patent
Kroeze et al.

(10) Patent No.: US 7,115,866 B1
(45) Date of Patent: Oct. 3, 2006

(54) SITE STEPPING FOR ELECTRON BEAM MICRO ANALYSIS

(75) Inventors: Roger Kroeze, San Francisco, CA (US); David A. Soltz, San Jose, CA (US); David A. Crewe, Sunnyvale, CA (US); Gregory W. Grant, San Jose, CA (US); Chiyan Kuan, Danville, CA (US); Thierry H. C. Nguyen, Sunnyvale, CA (US); Salvatore T. Fahey, Oakland, CA (US); Edward M. James, San Francisco, CA (US)

(73) Assignee: KLA-Tencor Technologies, Inc., Milpitas, CA (US)

( * ) Notice: Subject to any disclaimer, the term of this patent is extended or adjusted under 35 U.S.C. 154(b) by 0 days.

(21) Appl. No.: 11/116,617

(22) Filed: Apr. 28, 2005

(51) Int. Cl.
  *G21K 7/00* (2006.01)
  *G01N 23/00* (2006.01)
(52) U.S. Cl. .................. 250/310; 250/306; 250/307; 250/311
(58) Field of Classification Search ................ 250/307, 250/310
  See application file for complete search history.

(56) References Cited

U.S. PATENT DOCUMENTS

| | | | | |
|---|---|---|---|---|
| 4,243,866 A | * | 1/1981 | Pfeiffer et al. ........... 219/121.2 |
| 4,686,429 A | * | 8/1987 | Fendley ................. 315/368.12 |
| 4,818,885 A | * | 4/1989 | Davis et al. .............. 250/492.2 |
| 4,969,200 A | * | 11/1990 | Manns et al. ................ 382/288 |
| 5,481,109 A | * | 1/1996 | Ninomiya et al. ........... 250/310 |
| 5,867,902 A | * | 2/1999 | Minegishi et al. ........ 29/895.33 |
| 5,905,267 A | * | 5/1999 | Muraki ................... 250/492.22 |
| 5,933,217 A | * | 8/1999 | Nakasuji et al. ............... 355/53 |
| 6,373,071 B1 | * | 4/2002 | Innes et al. ............ 250/492.22 |
| 6,720,565 B1 | * | 4/2004 | Innes et al. ............ 250/492.22 |
| 6,849,859 B1 | * | 2/2005 | Folta et al. ............. 250/559.27 |
| 6,953,755 B1 | * | 10/2005 | Meyer et al. ................ 438/795 |
| 2001/0018153 A1 | * | 8/2001 | Irie .............................. 430/5 |
| 2002/0190207 A1 | * | 12/2002 | Levy et al. ................. 250/306 |
| 2004/0084632 A1 | * | 5/2004 | Komatsuda ............... 250/492.2 |
| 2005/0274911 A1 | * | 12/2005 | Aloni et al. ............ 250/492.22 |
| 2005/0282300 A1 | * | 12/2005 | Yun et al. ..................... 438/14 |

\* cited by examiner

*Primary Examiner*—John R. Lee
*Assistant Examiner*—Bernard Souw
(74) *Attorney, Agent, or Firm*—Luedeka, Neely, & Graham, P.C.

(57) ABSTRACT

A method of measuring properties of a sample using an electron beam. Coordinates of a measurement site on the sample, and a diameter of the electron beam are defined. Multiple measurement locations are determined within the measurement site, using the coordinates of the measurement site and the diameter of the electron beam. The measurement locations are selected such that the electron beam when directed at the multiple measurement locations (either through beam deflection or sample movement) substantially covers the measurement site. The electron beam is directed to the measurement locations and properties of the sample are measured at each of the measurement locations.

20 Claims, 3 Drawing Sheets

SITE STEPPING FOR ELECTRON BEAM MICRO ANALYSIS

FIELD

This invention relates to the field of integrated circuit fabrication. More particularly, this invention relates to electron beam measurement systems, such as are used to measure the parameters, such as thickness, of the layers of materials used in integrated circuits.

BACKGROUND

Integrated circuit fabrication is typically accomplished by forming many different layers on a substrate. As the term is used herein, "integrated circuit" includes devices such as those formed on monolithic semiconducting substrates, such as those formed of group IV materials like silicon or germanium, or group III–V compounds like gallium arsenide, indium phosphide, or mixtures of such materials. The term includes all types of devices formed, such as memory and logic, and all designs of such devices, such as MOS and bipolar. The term also comprehends applications such as flat panel displays, solar cells, and charge coupled devices.

Because the design tolerances of an integrated circuit are so strict, it is desirable to monitor the properties, such as thickness and elemental composition, of the various layers as they are formed. One way to measure the properties of film layers is to use a technique called electron stimulated x-ray metrology.

In very general terms, electron stimulated x-ray metrology works by directing a beam of electrons through a low pressure environment toward a sample surface. The electrons excite the atoms of the sample as they impinge against it. The excited atoms produce x-rays having properties that are characteristic of the properties of the sample, such as layer composition and layer thickness. Electron stimulated x-ray metrology is a highly favored technique, because in principle, it can be performed on production integrated circuits without damaging them.

Unfortunately, there are some problems with this and other techniques that employ electron beams. For example, deterioration of the x-ray signal over time, due to atom ejection, generally referred to as trending herein, requires that relatively short electron beam exposure times be used. However, a short acquisition time tends to result in a relatively low signal to noise ratio and large error bar spread.

What is needed, therefore, is a system that overcomes problems such as those described above, at least in part.

SUMMARY

The above and other needs are met by a method of measuring properties of a sample using an electron beam. Coordinates of a measurement site on the sample, and a diameter of the electron beam are defined. Multiple measurement locations are determined within the measurement site, using the coordinates of the measurement site and the diameter of the electron beam. The measurement locations are selected such that the electron beam when directed at the multiple measurement locations substantially covers the measurement site. The electron beam is directed to the measurement locations and properties of the sample are measured at each of the measurement locations.

In this manner, a system according to the present invention distributes the electron beam current over a clearly defined area. This can be a real advantage for confining the measurement to a specific feature inside of the scribe line on a production substrate. By spreading the beam over a larger area, total electron beam/sample interaction is reduced, trending is reduced, and the accuracy of the measurement is improved.

In various embodiments according to this aspect of the invention, the multiple measurement locations are determined such that no portion of the electron beam when directed at the multiple measurement locations extends outside of the measurement site. In one embodiment the electron beam is directed to the measurement locations by moving the electron beam relative to the substrate. In some embodiments the measured properties at the multiple measurement locations are averaged and reported. In another embodiment the electron beam is directed to the measurement locations by moving the substrate relative to the electron beam. This has the advantage of maintaining the proper positioning of detectors, such as those that collect X-rays, in the system relative to the electron beam. The advantage being that alignment and focus of the detectors is not compromised by the motion.

In one embodiment the multiple measurement locations are determined so as to maximize coverage of the measurement site with the electron beam. In an alternate embodiment the multiple measurement locations are determined so as to minimize trending effects of the electron beam within the measurement site. In yet another embodiment the multiple measurement locations are determined so as to provide a desired balance between increasing coverage of the measurement site with the electron beam and reducing trending effects of the electron beam within the measurement site. Preferably, the measured properties of the sample include at least one of layer thickness and layer composition. the sample is a substrate on which integrated circuits are formed.

According to another aspect of the invention there is described an apparatus for measuring properties of a sample. An electron beam functions as a measurement probe. An input receives coordinates of a measurement site on the sample, and a diameter of the electron beam. Means are provided to direct the electron beam toward the sample, and other means take measurements from the sample. Additional means move at least one of the electron beam and the sample relative to the other. A controller has programming modules to (1) determine multiple measurement locations within the measurement site using the coordinates of the measurement site and the diameter of the electron beam, which measurement locations are selected such that the electron beam when directed at the multiple measurement locations substantially covers the measurement site, (2) direct the electron beam to the measurement locations, and (3) measure properties of the sample at each of the measurement locations using the measurement means.

In various embodiments according to this aspect of the invention, the controller further has programming modules to determine the multiple measurement locations such that no portion of the electron beam when directed at the multiple measurement locations extends outside of the measurement site. In some embodiments, the controller further has programming modules to determine the multiple measurement locations so as to at least one of maximize coverage of the measurement site with the electron beam and minimize trending effects of the electron beam within the measurement site. In other embodiments, the controller further has programming modules to determine the multiple measurement locations so as to provide a desired balance between increasing coverage of the measurement site with the electron beam and reducing trending effects of the electron beam within the measurement site.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

Figure 1:
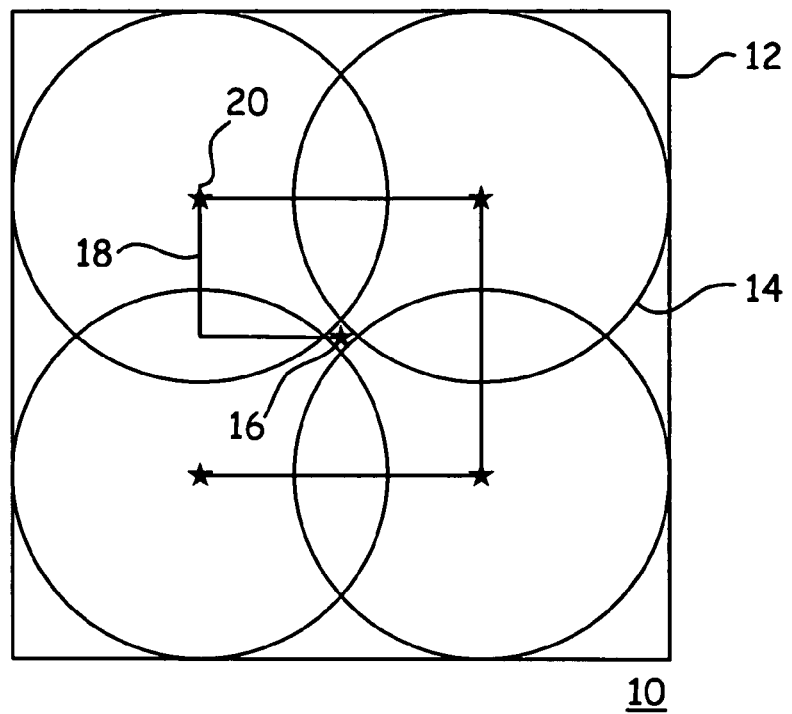
FIG. 1 is a depiction of a measurement pattern for a first beam size and a first measurement site size according to a first embodiment of the present invention.

FIG. 1 depicts a first embodiment of the present invention, where a measurement pattern 10 is produced within a measurement site 12, with beam locations 14. The measurement site 12 is a unitary, contiguous site, and does not have separate portions that are not all adjoined one to another. A plurality of beam locations 14 are preferably distributed within the measurement site 12, such as at spots 20, instead of at just a single location, such as center location 16, as was done in the prior art. By taking these several measurements within the measurement site 12, a better representation of the properties, such as thickness and composition, of the layers within the measurement site 12 can be made, without the trending that would tend to affect a reading that is taken in only a single location.

Figure 2:
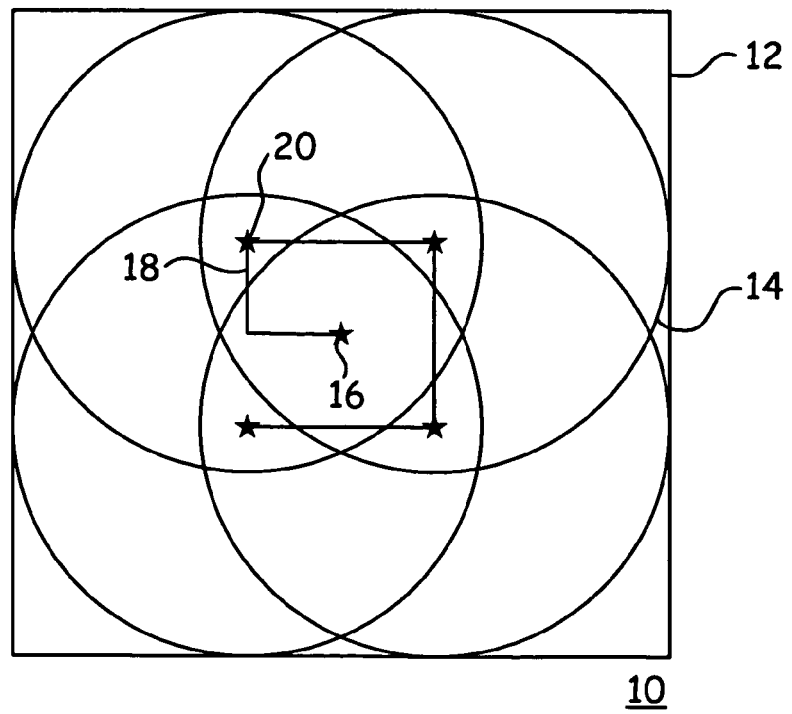
FIG. 2 is a depiction of a measurement pattern for a second beam size and a first measurement site size according to a second embodiment of the present invention.

According to the present invention, it is most preferred that a number of beam locations 14 be used which is sufficient to substantially completely cover the surface area of the measurement site 12, without undue overlap of the beam locations 14, such as is depicted in FIGS. 1 and 2. The balance between measuring as much of the measurement site 12 as possible and reducing overlap between the beam locations 14 can be set as desired, taking into consideration such parameters as the degree of trending that may be exhibited by the layers to be measured, and the amount of variation of the layer properties within the measurement site 12.

For example, if the layers exhibit a relatively large degree of trending and relatively small amount of variation, then a relatively reduced amount of overlap and a similarly relatively reduced percentage of measurement of the measurement site 12 may be desirable. On the other hand, if very little trending is anticipated, but a relatively large variation within the measurement site 12 is anticipated, then a relatively greater amount of overlap and a greater degree of coverage within the measurement site 12 may be preferred. Such balances of parameters can be empirically determined for the films to be measured, and menus of such parameter sets can be stored for later use.

In the example depicted in FIG. 1, a measurement site of about thirty-five microns square is selected, and a beam 14 diameter of about twenty microns is selected. In a preferred embodiment, the electron beam source and the stage on which the sample resides are under computerized control, and the stage is indexed so as to move the beam locations 14 along a path 18, so that measurements can be taken at the locations 20 indicated. The measurements so taken are then preferably averaged according to some desired method, such as a simple mean, and reported. The report may include variance statistics. Most preferably, none of the beam locations 14 extend outside of the measurement site 12.

FIG. 2 depicts an alternate embodiment where a larger beam 14 diameter is employed, such as about twenty-five microns. As depicted, the path 18 is preferably modified so as to provide different locations 20 at which to take the measurements. Most preferably, the beam 14 diameter can be specified by the user of the software. In some embodiments the user specifies the number of locations 20 at which measurements are to be taken, and the system determines where within the measurement site 12 those locations should be placed so as to produce a uniform coverage of the measurement site 12. Alternately, the system determines the number of measurement locations 20 to be used to provide a predetermined balance between measurement site 12 coverage beam location 14 overlap, as described above.

Most preferably, the user defines a measurement site 12 size, a beam 14 diameter, a measurement time, and the X and Y dimensions of the measurement array. The step size of the path 18 between the measurement locations 20 is calculated from the (measurement site 12 size/beam 14 diameter× number of measurement points in that axis), and the measurement time per point is determined from the (total measurement site time/number of points). After exposure of the initial point, the stage is moved to the second point 20 along the path 18, and so on, stepping across the entire measurement site 12. Current density is therefore evenly spread over the entire measurement site 12 area, and detector alignment and focus is maintained for the entire measurement.

In various embodiments, the beam scanning can be implemented using electrostatic or magnetic deflection, or beam defocus using objective lens, sample bias, gun lens, or intentional distortion of the electron beam, such as with astigmatism, coma, and blur. Stage or column mechanical vibration, or electromagnetic noise can also be used to intentionally blur the beam.

Figure 3:
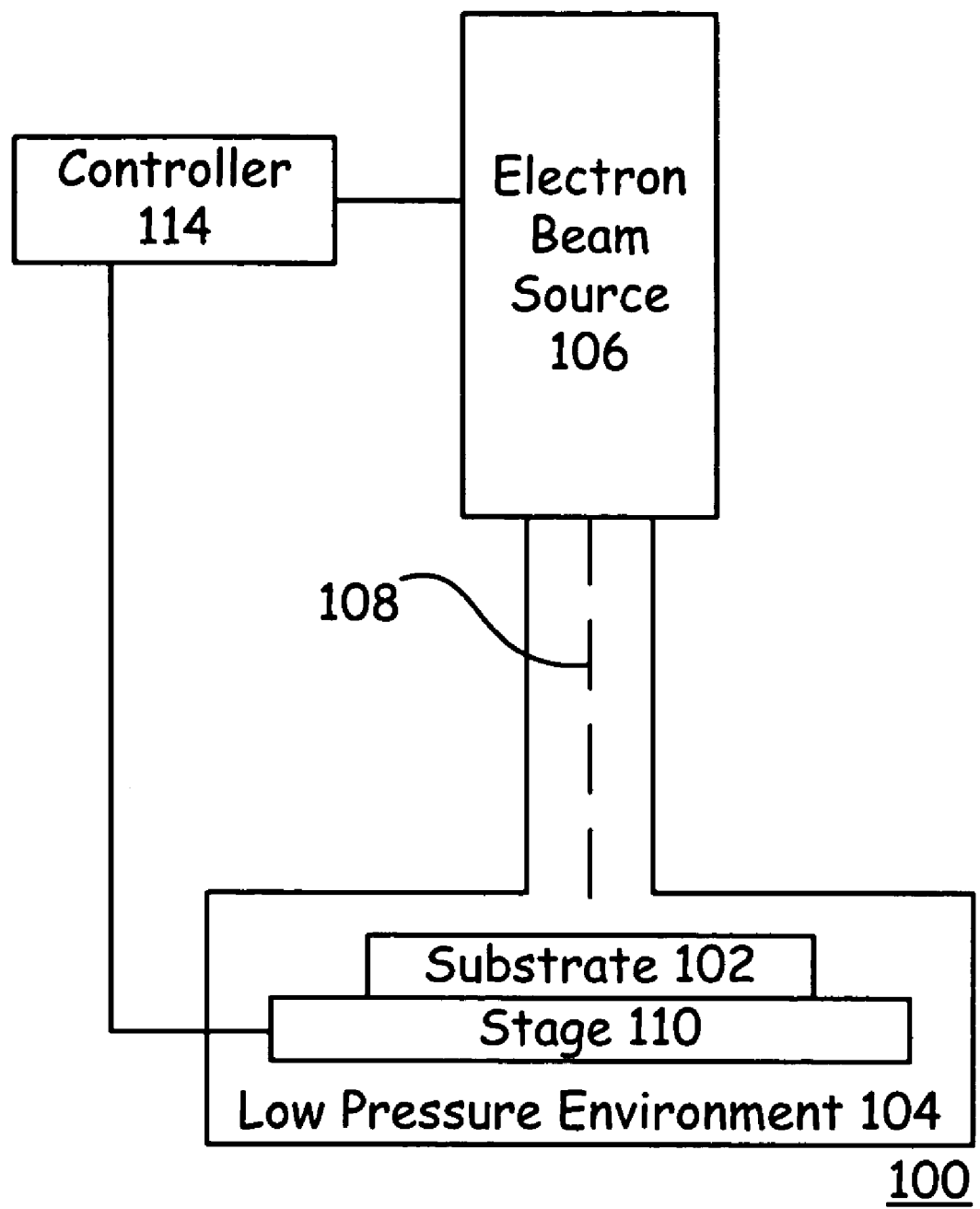
FIG. 3 is a functional block diagram of a system according to a preferred embodiment of the present invention.

With reference now to FIG. 3, there is depicted a functional block diagram of a system 100 according to a preferred embodiment of the present invention. The system 100 is preferably implanted such as in an electron stimulated x-ray metrology system, and thus includes the components and subsystems as are traditionally included with such systems, some of which are not depicted in FIG. 3 so as to more completely focus attention on the more novel aspects of the invention. The system 100 preferably includes an electron beam source 106 which directs an electron beam 108 toward the measurement site 14 on a substrate 102. Preferably, at least the electron beam 108 and the measurement site 14 of the substrate 102 are disposed within a low pressure environment 104.

As introduced above, the substrate 102 preferably resides on a stage 110. The stage 110, electron beam source 106, and other elements of the system 100 are preferably in communication with a controller 114. The controller 114 directs relative movement between the stage 110 and the electron beam source 106, so as to produce the measurement path 18 described above. As described, one or more of the electron beam source 106, the electron beam 108, and the stage 110 can be moved so as to provide the relative movement desired. The controller 114 preferably includes inputs and outputs for receiving instructions and providing readings, and memory for at least the temporary storage of such instructions and readings.

Figure 4:
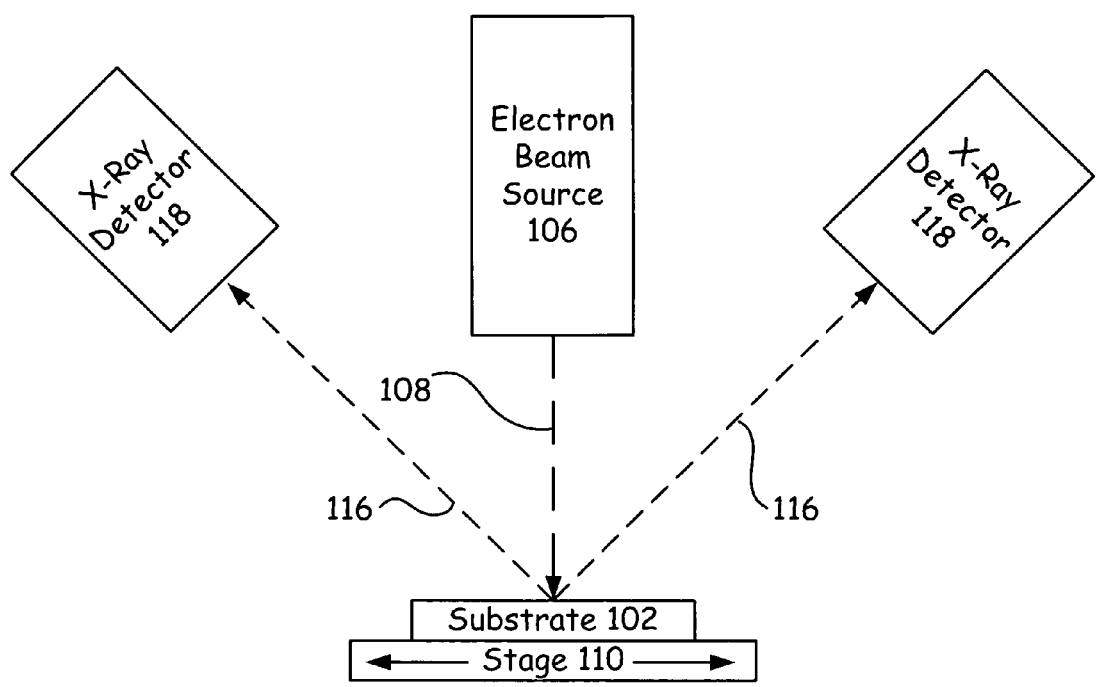
FIG. 4 Shows how site stepping will not compromise alignment and focus of the detectors during measurement.

FIG. 4 depicts a functional block diagram of the system 100, with an emphasis on some alternate components in comparison to the depiction of FIG. 3. FIG. 4 depicts X-ray signals 116 that are ejected by the substrate 102 when subjected to the electron beam 108. The X-ray signals 116 are preferably detected by X-ray detectors 118. As depicted, there is a benefit to moving the stage 110 to move to a different measurement site, instead of deflecting the electron beam 108 or otherwise moving the electron beam source 106, because the alignment and focus of the X-ray detectors 118 is not substantially altered when the stage 110 is moved. Thus, moving the stage 110 is the preferred method of moving from one measurement site to another.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of measuring properties of a sample using an electron beam, the method comprising the steps of:
    define coordinates of a measurement site on the sample,
    define a diameter of the electron beam,
    determine multiple measurement locations within the measurement site using the coordinates of the measurement site and the diameter of the electron beam, which measurement locations are selected such that the electron beam when directed at the multiple measurement locations substantially covers the measurement site, and
    direct the electron beam to the measurement locations and measure properties of the sample at each of the measurement locations based upon x-ray emission from the sample induced by the electron beam.

2. The method of claim 1, wherein the multiple measurement locations are determined such that no portion of the electron beam when directed at the multiple measurement locations extends outside of the measurement site.

3. The method of claim 1, wherein the electron beam is directed to the measurement locations by moving the substrate relative to the electron beam, thereby maintaining detector alignment and detector focus during multiple measurement operations and multiple measurement sites.

4. The method of claim 1, wherein the electron beam is directed to the measurement locations by moving the electron beam relative to the substrate.

5. The method of claim 1, wherein the measured properties at the multiple measurement locations are averaged and reported.

6. The method of claim 1, wherein the multiple measurement locations are determined so as to maximize coverage of the measurement site with the electron beam.

7. The method of claim 1, wherein the multiple measurement locations are determined so as to minimize trending effects of the electron beam within the measurement site.

8. The method of claim 1, wherein the multiple measurement locations are determined so as to provide a desired balance between increasing coverage of the measurement site with the electron beam and reducing trending effects of the electron beam within the measurement site.

9. The method of claim 1, wherein the measured properties of the sample include at least one of layer thickness and layer composition.

10. The method of claim 1, wherein the sample is a substrate on which integrated circuits are formed.

11. A method of measuring properties of a sample using an electron beam, the method comprising the steps of:
    define coordinates of a measurement site on the sample,
    define a diameter of the electron beam,
    determine multiple measurement locations within the measurement site using the coordinates of the measurement site and the diameter of the electron beam, which measurement locations are selected such that the electron beam when directed at the multiple measurement locations substantially covers the measurement site, wherein the multiple measurement locations are determined so as to provide a desired balance between increasing coverage of the measurement site with the electron beam and reducing trending effects of the electron beam within the measurement site, and no portion of the electron beam when directed at the multiple measurement locations extends outside of the measurement site, and
    direct the electron beam to the measurement locations and measure properties of the sample at each of the measurement locations based upon x-ray emmission from the sample induced by the electron beam.

12. The method of claim 11, wherein the electron beam is directed to the measurement locations by moving the substrate relative to the electron beam, thereby maintaining detector alignment and detector focus during multiple measurement operations and multiple measurement sites.

13. The method of claim 11, wherein the electron beam is directed to the measurement locations by moving the electron beam relative to the substrate.

14. The method of claim 11, wherein the measured properties at the multiple measurement locations are averaged and reported.

15. The method of claim 11, wherein the measured properties of the sample include at least one of layer thickness and layer composition.

16. The method of claim 11, wherein the sample is a substrate on which integrated circuits are formed.

17. An apparatus for measuring properties of a sample, the apparatus comprising:
    an electron beam adapted to function as a measurement probe,
    an input adapted to receive coordinates of a measurement site on the sample, and a diameter of the electron beam,
    means to direct the electron beam toward the sample,
    means to take measurements from sample based upon x-ray emission from the sample induced by the electron beam,
    means for moving at least one of the electron beam and the sample relative to the other, and a controller having programming modules to,
    determine multiple measurement locations within the measurement site using the coordinates of the measurement site and the diameter of the electron beam, which measurement locations are selected such that the electron beam when directed at the multiple measurement locations substantially covers the measurement site,
    direct the electron beam to the measurement locations, and
    measure properties of the sample at each of the measurement locations using the measurement means.

18. The apparatus of claim 17, wherein the controller further has programming modules to determine the multiple measurement locations such that no portion of the electron beam when directed at the multiple measurement locations extends outside of the measurement site.

19. The apparatus of claim 17, wherein the controller further has programming modules to determine the multiple measurement locations so as to at least one of maximize coverage of the measurement site with the electron beam and minimize trending effects of the electron beam within the measurement site.

20. The apparatus of claim 17, wherein the controller further has programming modules to determine the multiple measurement locations so as to provide a desired balance between increasing coverage of the measurement site with the electron beam and reducing trending effects of the electron beam within the measurement site.

* * * * *